(12) United States Patent
Beerens et al.

(10) Patent No.: US 11,679,010 B2
(45) Date of Patent: Jun. 20, 2023

(54) ADAPTOR FOR MOUNTING A PROSTHESIS

(71) Applicant: Xilloc Nexus B.V., Geleen (NL)

(72) Inventors: Maikel Michael Adrianus Beerens, Geleen (NL); Harry Christiaan Antoon Jansen, Wijchen (NL)

(73) Assignee: Xilloc Holding B.V., Geleen (NL)

( * ) Notice: Subject to any disclaimer, the term of this patent is extended or adjusted under 35 U.S.C. 154(b) by 513 days.

(21) Appl. No.: 16/970,730

(22) PCT Filed: Feb. 20, 2019

(86) PCT No.: PCT/NL2019/050113
§ 371 (c)(1),
(2) Date: Aug. 18, 2020

(87) PCT Pub. No.: WO2019/164394
PCT Pub. Date: Aug. 29, 2019

(65) Prior Publication Data
US 2020/0368041 A1 Nov. 26, 2020

(30) Foreign Application Priority Data
Feb. 20, 2018 (NL) ................................ NL2020464

(51) Int. Cl.
*A61F 2/78* (2006.01)
*A61F 2/30* (2006.01)

(52) U.S. Cl.
CPC ...... *A61F 2/78* (2013.01); *A61F 2002/30495* (2013.01)

(58) Field of Classification Search
CPC .... A61F 2/76; A61F 2002/30495; A61F 2/75; A61F 2/78; A61F 2002/5083
See application file for complete search history.

(56) References Cited

U.S. PATENT DOCUMENTS 9,572,689 B2   2/2017   Ossur

FOREIGN PATENT DOCUMENTS

| NL | 2010991 | 12/2014 | |
| NL | 2010991 C | * 12/2014 | ............... A61F 2/76 |
| WO | 2007018904 | 2/2007 | |
| WO | 2013079091 | 6/2013 | |

* cited by examiner

*Primary Examiner* — Kevin T Truong
*Assistant Examiner* — Diana Jones
(74) *Attorney, Agent, or Firm* — Marcus C. Dawes

(57) ABSTRACT

The present invention relates to an adaptor for mounting a prosthesis to a prosthetic pin that protrudes from a user's body. The adaptor comprises a male part coupled to a prosthetic pin, a female part coupled to the prosthesis and to the male part, and a locking ring for locking a rotation of the male part relative to the female part. According to the invention, the female part further comprises an at least partially resilient bush arranged in the female part that is configured to expand in a radial direction when the bush is compressed in an axial direction to lock a rotation of the male part relative to the female part.

19 Claims, 11 Drawing Sheets

ADAPTOR FOR MOUNTING A PROSTHESIS

The present invention relates to an adaptor for mounting a prosthesis to a prosthetic pin that protrudes from a user's body. The invention particularly relates to the medical field of osseointegration in which a direct interface is formed between an implant and bone, without intervening soft tissue.

In the field of osseointegration, a pin or other implant is implanted into a bone of a limb of the patient to which the prosthesis should be connected to. The pin, which is normally made from metals such as Titanium, integrates with the hone structure. After sufficient integration and fixation, a prosthesis can be attached to the pin.

Adaptors used for mounting a prosthesis to a prosthetic pin are known in the art. An example of such an adaptor is found in Dutch patent NL2010991. This adaptor comprises a female part and a male part, wherein the female part is configured to be coupled to the prosthesis and wherein the male part is configured to be coupled to the prosthetic pin.

The known adaptor comprises axial locking means for releasably and axially locking the male part and female part relative to each other. It further comprises rotational locking means for rotationally locking the male part and female part relative to each other. In the known adaptor, the rotational locking means comprise a breaking device that is configured to break when an externally applied torque between the male part and female part exceeds a predetermined level thereby allowing the female part and the male part to rotate with respect to each other.

The known adaptor offers the advantage that it can be ensured that the rotational locking means will disengage when excessive torque is applied, while the adaptor is still able to guarantee sufficient axial locking during normal use.

However, a drawback of the known adaptor is that the user should visit an osseointegration specialist to replace the breaking device if this device breaks under excessive torque. In the meantime, the user cannot use the adaptor causing inconvenience to the user, particularly if the unfortunate event does not occur during office hours or not within reach of an osseointegration specialist.

It is an object of the present invention to provide a solution to this problem. According to the invention, this object is achieved using the adaptor as defined in claim 1, which comprises a male part configured to be coupled to a prosthetic pin that protrudes from a user's body, and a female part that is configured to be coupled to the prosthesis and to the male part, and which female part comprises an elongated cavity. The adaptor further comprises a locking element in the form of a locking ring for locking a rotation of the male part relative to the female part.

The adaptor according to the invention is characterized in that the female part further comprises an at least partially resilient bush arranged in the cavity and being configured to expand in a radial direction when the bush is compressed in an axial direction. The male part can be arranged in or through the bush. Furthermore, the locking ring is configured to compress the bush in the axial direction such that the bush expands in the radial direction to thereby lock a rotation of the male part relative to the female part.

When rotationally locked, the resilient bush pushes against the inner wall and the male part. Consequently, any rotation between the male part and female part is subjected to frictional forces that increase with the pushing force exerted by the resilient bush onto the male part. If the torque between the male part and the female part becomes too large, the frictional forces will be overcome and the male part will rotate relative to the female part. For example, the bush may remain stationary relative to the inner wall of the cavity while the male part rotates relative to the bush, or the bush may rotate relative to the inner wall of the cavity while the male part remains stationary relative to the bush, or the bush may rotate relative to the inner wall of the cavity while the male part rotates relative to the bush. In all cases, and contrary to the known adaptor, no components will break during the rotation allowing the user to re-align the male part and the female part after the incident and to continue his or her activities. An additional beneficial effect is related to the damping of oscillations between the male part and the female part by the resilient bush.

The locking ring may be coupled to the female part, and it may be movable between a first position, in which position the locking ring exerts no or a relatively low force in the axial direction onto the bush, and a second position, in which the locking ring compresses the bush in the axial direction for said locking of a rotation of the male part relative to the female part. A user may bring the locking ring in the first position to allow the user to align the male part and the female part, and to then bring the locking ring in the second position to fix the angular position of the male part relative to the female part.

The locking ring preferably pushes in an axial direction onto the bush. For example, the coupling of the locking ring to the female part may be such that a rotation of the locking ring relative to the female part causes an axial displacement of the locking ring relative to the female part to thereby increase or decrease the compression of the bush. For example, the rotation of the locking ring may follow a spiraling path around an outer wall of the female part. Typically, the amount of rotation of the locking ring required to move between the first and second position is less than a full revolution around the axial axis of the female part.

The outer wall of the female part may comprise one or more guiding tracks. Moreover, the locking ring may comprise one or more radially inwardly extending guiding elements which are each guided in one of said guiding tracks. The locking ring may further comprise one or more pushing elements for pushing in an axial direction onto the bush. Alternatively, the one or more pushing elements can be formed by an inner wall of the locking ring. The one or more guiding tracks may each comprise a spirally extending recess defined in the outer surface of the female part. Hence, when the locking ring is rotated from the first position to the second position, the locking ring is also moved in axial direction by the guiding elements that follow the guiding track that spirals down away from the locking ring. At the same time, the pushing elements push more and more onto the bush.

The adaptor may further comprise a further resilient element arranged in between the one or more pushing elements and the resilient bush. The further resilient element has a lower modulus of elasticity, more preferably a lower Young's modulus, in the axial direction of the female part than in the radial direction. Consequently, the further resilient element can be compressed in the axial direction, by the one or more pushing elements. The further resilient element may comprise at least one of a wave spring, a multi-wave spring, and a nested wave spring.

To prevent the locking ring from moving from the second position to the first position under the influence of the resiliency of the bush the adaptor may comprise a lock for locking movement of the locking ring in the second position.

The lock may additionally or alternatively be configured for locking the movement of the locking ring in the first position.

The lock may comprise a locking pin having a recessed portion and a non-recessed portion. The locking pin may be mounted in an axial direction in the locking ring. For example, the locking ring may be mounted in a top surface of the locking ring. The lock may further comprise a spring for spring biasing the locking pin to urge the locking pin to move in an axial direction. Preferably, the spring biasing is such that the locking pin is urged to extend from the top surface allowing a user to operate the locking pin.

The movement of the locking pin as a function of the angular position of the male part relative to the female part is defined by a locking track that is arranged on an outer wall of the female part. The locking track may comprise a radially protruding edge having an open portion. Here, an open portion of the locking track relates to a portion in which no edge is present or wherein the edge does not protrude to the same extent as in other portions of the locking track. When moving the locking ring between the first and second position, the recessed portion engages the locking track. When the locking ring reaches the second position, the spring causes the locking pin to move in the axial direction such that the recessed portion no longer engages the locking track and the non-recessed portion abuts the locking track, thereby preventing a rotation of the locking ring from the second position to the first position. When the locking ring is in the second position, the locking pin may be configured to protrude from an upper surface of the locking ring. in this case, the locking pin can be pushed in the axial direction to bring the recessed portion back into alignment with the locking track thereby allowing the locking ring to be moved from the second position to the first position.

The outer wall of the female part may comprise a radially protruding blocking element. When the locking ring moves from the second to the first position, rotation beyond the first position is prevented by the locking pin engaging the blocking element.

The guiding track may comprise an open portion that allows the locking ring to be separated from the female part by moving the guiding elements in an axial direction through the open portions of the guiding track and away from the female part. However, the radially protruding blocking element may be arranged such that when moving the locking ring from the second position to the first position, a position in which the guiding elements reach the open portion of the guiding track cannot be reached due to the locking pin being blocked by the protruding blocking element.

Alternatively, the lock may comprise a positioning element mounted in a radial direction in the locking ring, wherein the positioning element comprises a positioning pin, and a spring for spring biasing the positioning pin to move outwardly. The female part may comprise an edge having a first recess and a second recess corresponding the first and second position, respectively. The positioning pin may comprise a protruding end. When the locking ring is in the first or second position, the positioning pin moves outwardly to engage the first or second recess, respectively, to lock the locking ring in the first or second position, respectively. Moreover, when the locking ring is in an intermediate position between the first and second position, the protruding end is guided in between an inner wall of the female part and said edge.

The female part may comprise a circumferential locking groove, and the locking ring may comprise a locking pin that protrudes through the locking ring and into the circumferential groove, the circumferential groove and locking pin being configured to limit the rotation of the locking ring relative to the female part to prevent the locking ring from getting detached from the female part while the locking pin engages the locking groove.

The cavity in the female part may comprise a first part, which exits on an outer surface of the female part facing the locking ring, and a second part adjoining the first part in the axial direction, wherein the first part is wider than the second part, and wherein a transition from the inner wall of the first part to the inner wall of the second part defines a support surface for supporting the bush. For example, the inner wall of the female part may have an edge or rim near or forming the interface between the first and second parts.

The bush may comprise a ring assembly that comprises a plurality of first and second rings, wherein the first rings are made from essentially rigid material and wherein the second rings are made from essentially resilient material. The first plurality of rings may comprise one or more substantially identical rings and a calibration ring. In some embodiments, the axial displacement of the locking ring may be substantially identical regardless of the thickness of the calibration ring. However, by increasing the thickness of the calibration ring, more force will be exerted onto the bush compared to a thinner ring. As such, the maximum torque that can be applied to the adaptor can be set for example in dependence on the height and/or weight of the user and/or the type of activities of the user.

The ring assembly may further comprise a plurality of third rings made from essentially resilient material having a different shore hardness than the second rings. By varying the shore hardness of the second and/or third rings and/or by changing the relative number of these rings in the ring assembly, the maximum torque can be changed. This is related to the different coefficients of friction associated with the different materials used for the second and/or third rings.

The female part may comprise an alignment pin. Moreover, the male part may have an alignment cavity or recess, wherein the alignment pin is configured to engage the recess or cavity for a given angular orientation of the male part relative to the female part. The alignment pin can be spring biased to move radially inward into the second part of the cavity, and the alignment pin can be configured to move into the recess or cavity for said given angular orientation of the male part relative to the female part.

The alignment pin allows a user to conveniently position the female part and the male part relative to each other when placing the male part into the female part. In some embodiments, the user may notice a clicking sound that is associated with the alignment pin extending into the alignment recess of cavity and/or may feel the movement of the alignment pin. It should be noted that the alignment pin and recess constitute a further lock of rotational movement of the male part relative to the female part although the associated locking force is considerably smaller than the locking force associated with the ring assembly.

The male part may comprise a cavity in which the prosthetic pin can be arranged, a radially inwardly extending edge or rim, and a mounting unit, such as a bolt, wherein the mounting unit can be coupled to an inner opening of the prosthetic pin such that an outer end of the mounting unit engages the extending edge or rim for locking a movement in a first direction of the male part relative to the prosthetic pin. The prosthetic pin may have a tapered outer shape that matches an inner wall of the male part such that the male part can be form fitted onto the prosthetic pin such that further movement of the male part and the female part in a second direction opposite to the first direction is blocked. The combination of this form fitting locking and locking by the mounting unit enables the male part to be coupled to the prosthetic pin.

Next, the invention will be described in more detail referring to the appended drawings, wherein.

Figure 1:
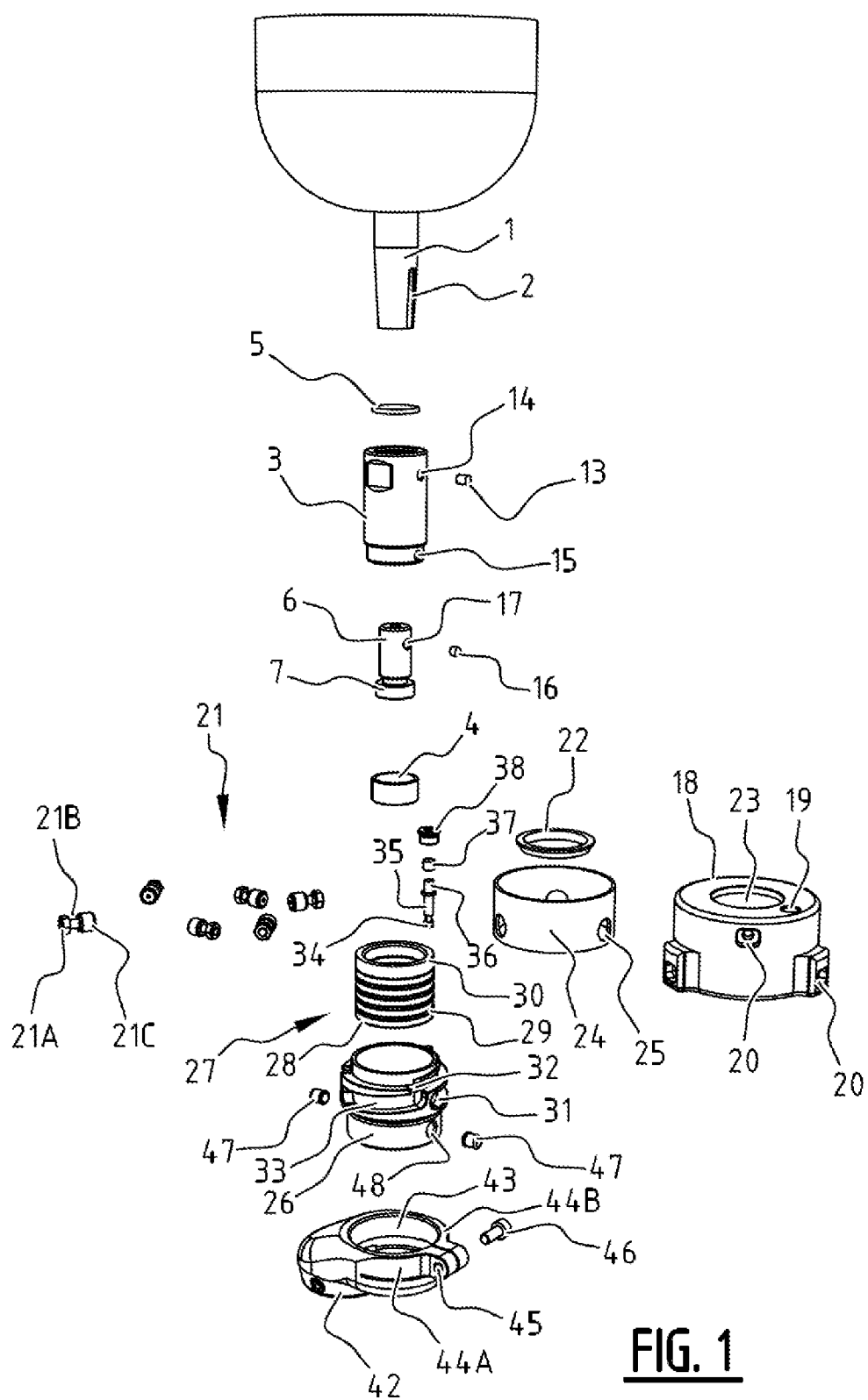
FIG. 1 illustrates an exploded view of an embodiment of the adapter in accordance with the present invention.

FIG. 1 illustrates an exploded view of an embodiment of the adapter in accordance with the present invention. FIG. 1 further shows a substantially cylindrical pin 1 that protrudes from a body part, e.g. upper leg, of the user. Pin 1 has a tapered end such that the external diameter of the pin decreases toward the end. Pin 1 further comprises an alignment recess 2.

Figure 2:
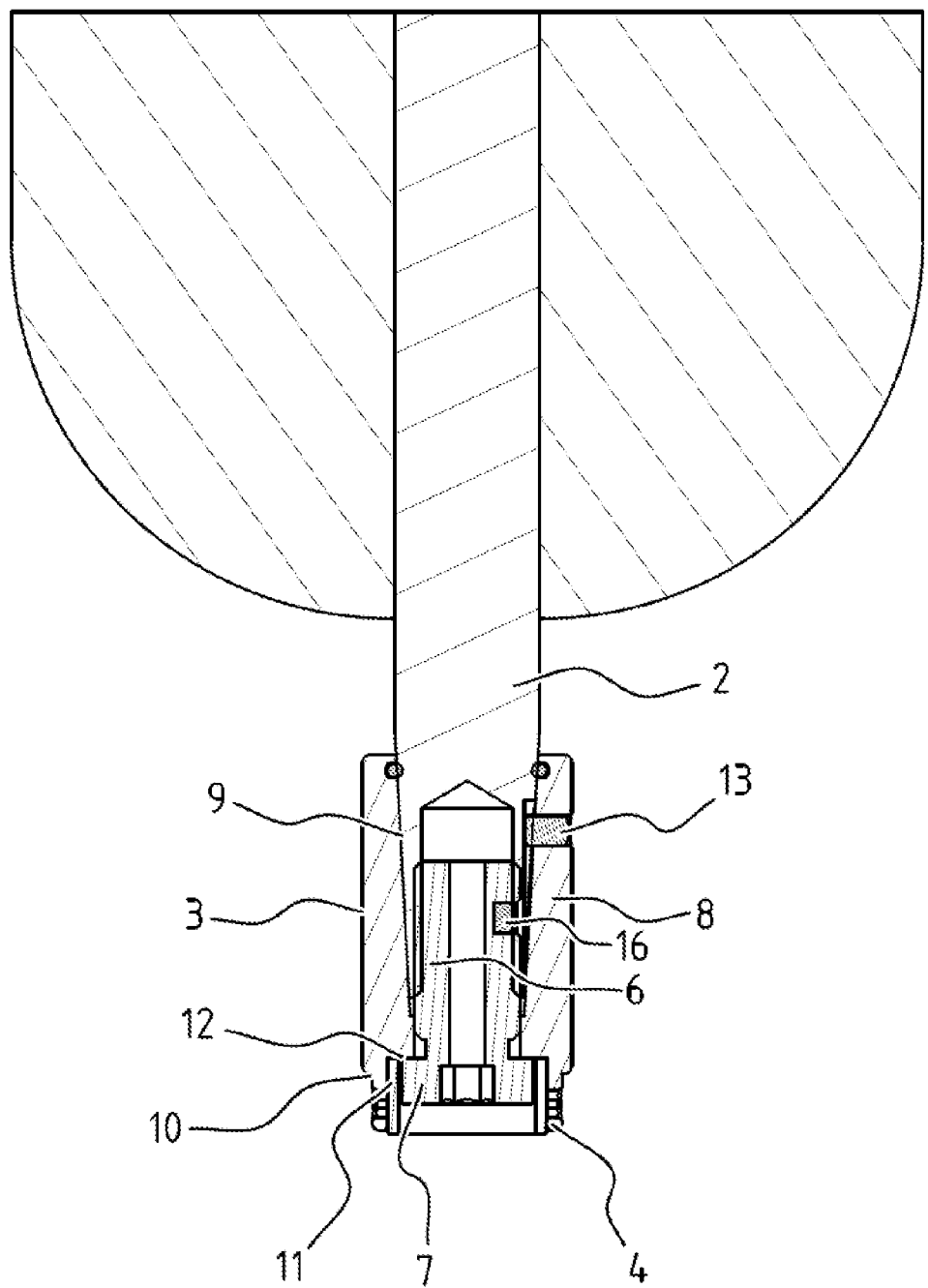
FIG. 2 illustrates a cross sectional view of the male part of the embodiment in FIG. 1.

The adaptor of the invention comprises a male part consisting of a substantially cylindrical male body 3, a sleeve 4, a ring 5, and a mounting unit, which in FIG. 1 is embodied as a bolt 6 having a bolt head 7. As can be seen in FIG. 2, a first part 8 of the inner wall of body 3 defines a first cavity 9 of which the wall matches the tapered form of pin 1. The second part 10 of the inner wall defines a second cavity 11 that has a larger diameter than first cavity 9. The transition between parts 8 and 10 defines an edge or rim 12 that can be seen in FIG. 2.

The male part can be coupled to pin 1 by arranging body 3 over pin 1 such that pin 1 is received in first cavity 9 in a form fitted manner. More in particular, first part 8 of the inner wall of body 3 abuts the tapered outer end of pin 1 thereby preventing body 3 to slide even further over pin 1. To secure body 3 to pin 1, at least to prevent it from sliding off pin 1, bolt 6 is arranged through second cavity 11. More in particular, pin 1 has at its end an internal cavity of which the walls are provided with screw thread. A corresponding threading is applied on the outer surface of bolt 6. This allows bolt 6 to be screwed into pin 1. By doing so, bolt head 7 will at a given moment engage rim 12 thereby pushing body 3 upwards.

Ring 5, which may be of resilient material, can be used to provide a sealing function. Furthermore, as can be seen in FIG. 2, sleeve 4 is arranged in between bolt head 7 and second part 10 of the inner wall of body 3. It extends only slightly beyond body 3 to prevent direct contact between body 3 and the female part as will be discussed later.

To facilitate proper alignment of body 3 relative to pin 1, alignment pin 13, which may or may not be spring biased, penetrates through opening 14 into recess 2 if recess 2 and opening 14 are aligned. To facilitate proper alignment of body 3 relative to the actual prosthesis, one or more alignment recesses 15 are provided on the outer surface of body 3.

Element 16 is a deformable object that is arranged in opening 17 of bolt 6. When screwing bolt 6 into pin 1, element 16 will deform thereby realizing a clamping between bolt 6 and pin 1 preventing or limiting the inadvertent decoupling of bolt 6 and pin 1.

The adapter further comprises a locking ring 18, which is provided at an upper side thereof with a locking opening 19. A side surface of locking ring 18 is provided with a plurality of openings 20 through which elements 21 are inserted. In the embodiment shown in FIG. 1, openings 20 are provided at two height levels of the side surface.

FIG. 1 illustrates elements 21 in assembled form. These elements each comprise a mounting element 21A, which can be form-fitted in openings 20, and a pin element 21B around which a bushing 21C is provided. Each element 21 further comprises a bearing allowing bushing 21C to be rotated relative to pin element 21B. Furthermore, pin element 21B can be mounted in mounting element 21A, for example using a threaded coupling.

The adapter further comprises a slide bearing 22 made from any suitable sealing material such as rubber. Slide bearing 22 may be fitted into an opening 23 in locking ring 18 and prevents direct contact between pin 3 and locking ring 18. More in particular, slide bearing 22 may rest on a rim or edge of locking ring 23. In addition to slide bearing 22, the adapter may further comprise a slide bearing 24 that is to be inserted in locking ring 18 and which prevents direct contact between female part 26 and locking ring 18. This is shown in more detail in FIG. 3A.

Figure 3A:
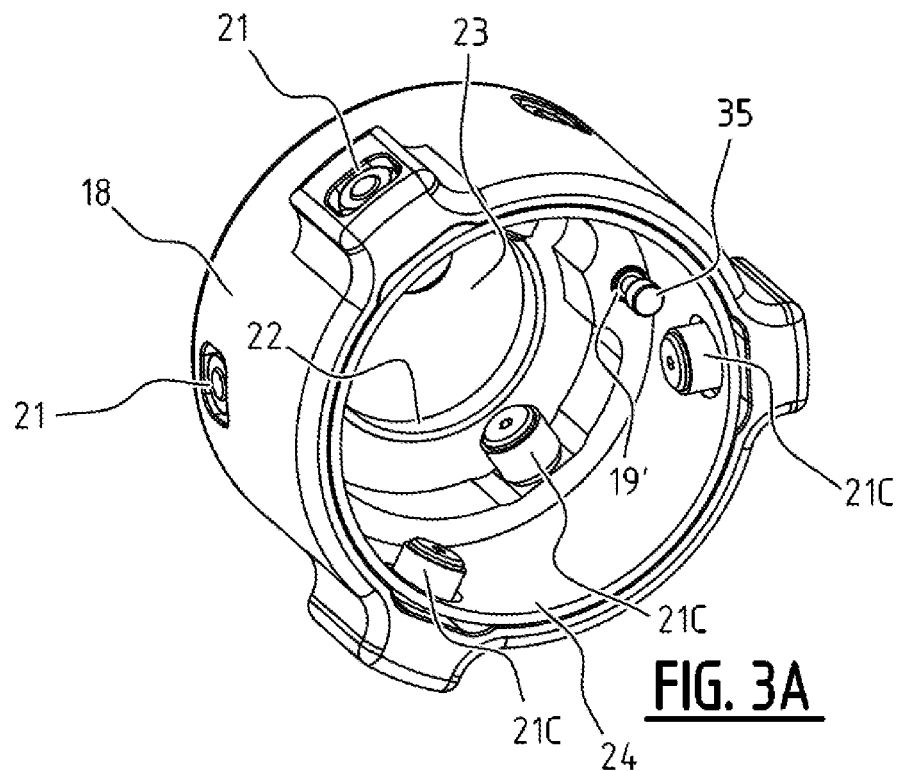
FIGS. 3A and 3B illustrate perspective views of the locking ring of the adapter of FIG. 1.
Figure 3B:
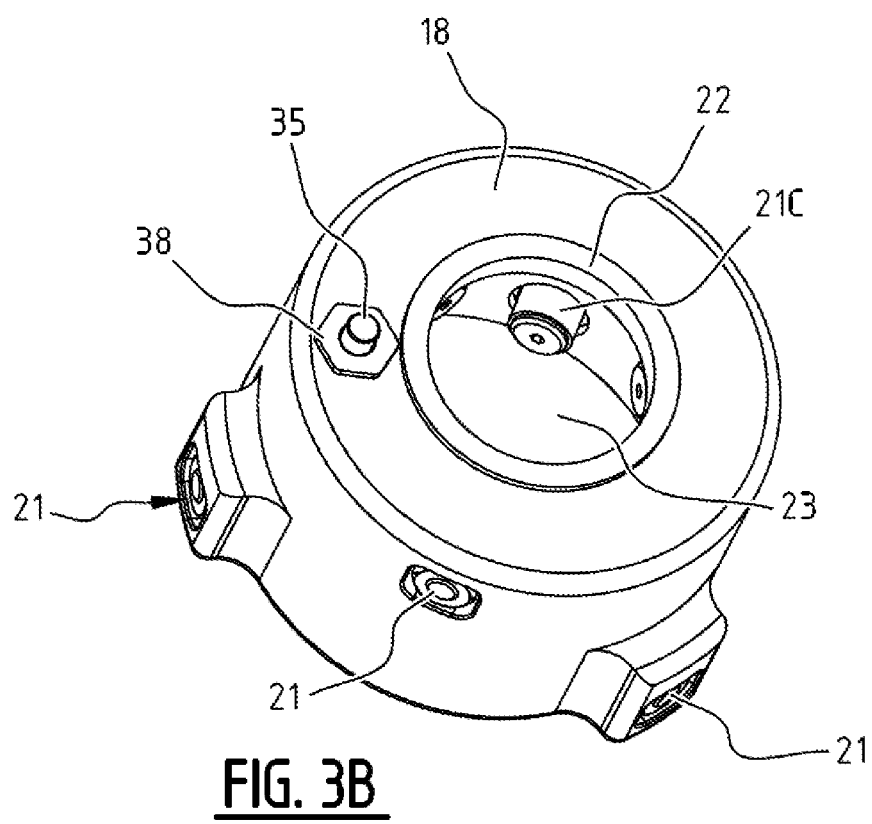

FIG. 3A illustrates locking ring 18 from a bottom side, wherein elements 21, slide bearing 22, and slide bearing 24 are mounted in locking ring 18. As illustrated in FIG. 1, slide bearing 24 may comprise one or more openings 25 that correspond to those openings 20 in the side surface of locking ring 18 that are arranged near a bottom side of locking ring 18. For the embodiment in FIG. 1, only the lower three openings 20 are aligned with openings 25. Slide bearing 24 may be fixed relative to locking ring 18 by pressing slide bearing 24 into locking ring 18 after having aligned openings 25 with openings 20. Thereafter, mounting elements 21A are placed in openings 20 in the side surface of locking ring 18 from an outside thereof. As a next step, pin elements 21B with bushings 21C are mounted from the inside of locking ring 18 through openings 25 when applicable, and through openings 20, to mounting elements 21A arranged in openings 20.

Hereinafter, elements 21 which penetrate the lower openings 20 and openings 25 will be designated as guiding elements whereas the remaining elements 21 will be designated as pushing elements.

The adapter further comprises a female part 26 that is configured to the male part. Inside female part 26, a ring assembly 27 is arranged. This assembly comprises a plurality of first 28 and second rings 29, wherein the first rings are made from a substantially non-resilient material such as stainless steel and wherein the second rings are made from a resilient material such as rubber. A separate non-resilient end ring 30, having dimensions different from those of first rings 28 and referred to as calibration ring, may be arranged on a top side of ring assembly 27.

Figure 4:
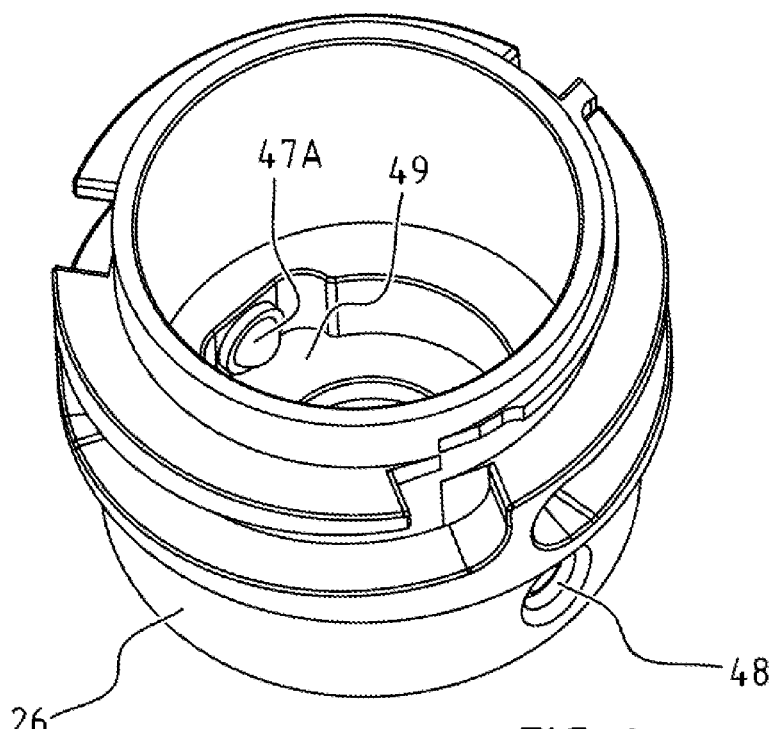
FIG. 4 illustrates a perspective view of the female part of the adapter of FIG. 1.

When placed in female part 26, ring assembly 27 may rest on a bottom wall 49 of female part 26, as illustrated in FIG. 4. Furthermore, near bottom wall 49, female part 26 may be provided with a plurality of through openings 48. In these openings 48, an alignment pin 47 may be mounted under spring bias such that it extends radially inward. FIG. 4 presents an example of such an alignment pin 47.

On a side surface of female part 26, a plurality of guiding tracks 31 is formed, each track 31 comprising a vertical portion 32 extending downwardly from an upper surface of female part 26, and a circumferential portion 33 that partially extends around a side surface of female part 26 in a spiraled manner, see FIG. 4. Guiding tracks 31 may be formed by recessing the side surface of female part 26.

Locking ring 18, having slide bearing 22 and slide bearing 24 mounted thereto, can be coupled to female part 26. To that end, bushings 21C of guiding elements 21 are aligned with vertical portions 32. Thereafter, locking ring 18 is moved downwardly so that each bushing 21C of lower elements 21 engages a respective vertical portion 32 and becomes guided thereby. When the lowest point of vertical portion 32 is reached, locking ring 18 is rotated such that each bushing 21C of lower elements 21 engages a respective circumferential portion 31 and becomes guided thereby. When locking ring 18 rotates, spiral guiding track 31 will induce an axial displacement of locking ring 18. This will cause pushing elements 21 to exert more or less force on ring assembly 27.

To prevent locking ring 18 to become inadvertently disengaged from female part 26, a locking pin can be arranged through opening 19 of locking ring 18. The locking pin comprises a recessed portion 34, a non-recessed portion 35, and a rim 36. The locking pin can be mounted in locking ring 18 in a spring biased manner using spring 37 and mounting element 38. More in particular, to mount the locking pin in locking ring 18, spring 37 is mounted on the locking pin below rim 36. When locking ring 18 and spring 37 are arranged in opening 19, spring 37 rests against an inner surface of locking ring 18 as it cannot, unlike the locking pin, penetrate opening 19', which is arranged opposite to opening 19 and which is shown in FIG. 3A. Spring 37 pushes against rim 36. The actual biasing of the locking pin occurs by arranging mounting element 38 in opening 19. As rim 36 cannot pass through mounting element 38, the locking pin remains mounted in locking ring 18.

The outer surface of female part 26 comprises a locking track 39, which extends in a spiral manner substantially parallel to circumferential portion 31. Locking track 39 and its interplay with the locking pin is shown in more detail in FIGS. 5A-5C, wherein only the locking pin and female part 26 are shown. Here, it is shown that once the locking pin is mounted in locking ring 18, its recessed portion 34 engages locking track 39. As such, when rotating locking ring 18, the position of the locking pin will be determined by locking track 39.

Figure 5A:
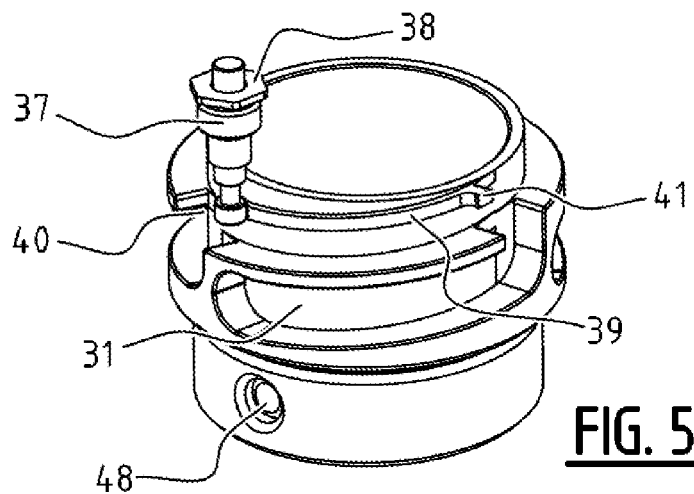
FIGS. 5A-5C illustrate top side perspective views of the locking ring of the adapter of FIG. 1 coupled to the female part.

Because locking track 39 extends substantially parallel to guiding track 31, a rotation of locking ring 18 will not substantially affect the relative position of the locking pin in locking ring 18. However, at the end of locking track 39 an open portion 40 is provided. When locking ring 18 is rotated such that locking pin enters the open portion 40, the locking pin will move upwards under the influence of the spring force exerted by spring 37. Thereafter, non-recessed portion 35 will abut locking track 39, thereby preventing the rotation of locking ring 18 at least in one direction. This situation is shown in FIG. 5A, with the position of locking pin only just prior to reaching open portion 40 being illustrated in FIG. 5B.

In general, the position at which locking pin enters open portion 40 corresponds to the second position of locking ring 18, which corresponds to the position in which guiding elements 21 have reached the end of their corresponding guiding track 31. Without the upward motion of the locking pin, locking ring 18 would rotate in reverse direction due to the spring force related to the compression of ring assembly 27.

Figure 5B:
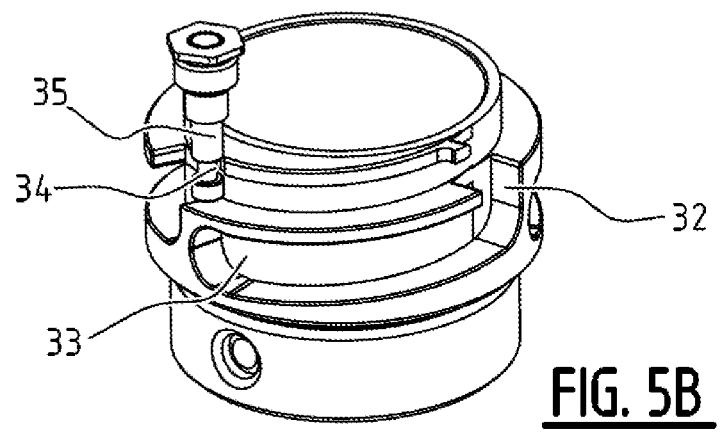
Figure 5C:
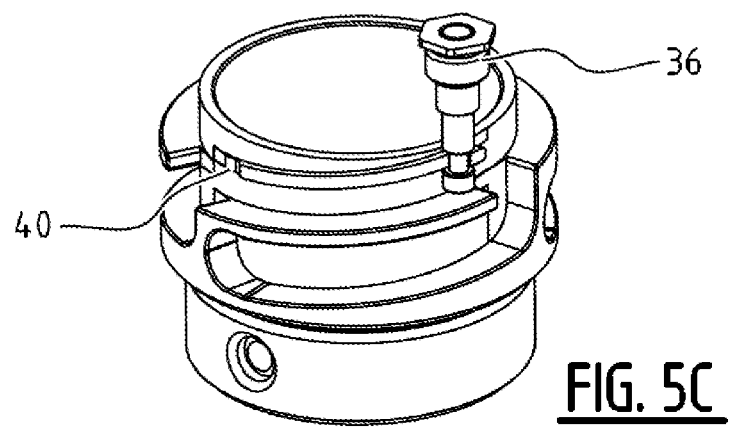

To be able to rotate locking ring 18 back to a position in which pushing elements 21 do not exert a substantial compressive force on ring assembly 27, a user has to push on the top end of the locking pin against the spring force to bring recessed portion 34 back into alignment with locking track 39 as shown in FIG. 5B. Thereafter, the user, while still pressing on the locking pin, may rotate locking ring 18. Once recessed portion 34 again engages locking track 39 the user may stop pushing on the locking pin.

Further rotation of locking ring 18 is eventually stopped by a radially protruding blocking element 41. This will at some point engage recessed portion 34 in such a manner that locking ring 18 cannot rotate further. This position of locking ring 18 corresponds to the first position.

As may be appreciated from the discussion above, the locking pin can only be mounted in locking ring 18 if locking ring 18 is in the second position. Only in this position, the locking pin may be arranged through openings 19, 19' without being blocked by locking track 39.

Female part 26 may be coupled to an adapter plate 42. To this end, adapter plate 42 is provided with an inner opening 43 having a threaded wall. A similar threaded wall may be provided on a lower portion of the side surface of female part 26 allowing both components to be coupled. Opening 43 may be formed using two semi-circular ring parts 44A, 44B that are spaced apart at one end of adapter plate 43. Here, each ring part may be provided with an opening 45. By arranging a suitable clamping through openings 45, e.g. using a bolt 46, ring parts 44A, 44B can be clamped thereby allowing a further coupling mechanism between female part 26 and adapter plate 42. In an embodiment, female part 26 is first inserted in opening 43 and coupled thereto by rotating female part 26 relative to opening 43. After female part 26 and adapter plate 42 are properly aligned, ring parts 44A, 44B are clamped together, thereby fully fixing the mutual position of female part 26 and adapter plate 42. Such alignment is important as adapter plate 42 is attached to the actual prosthesis (not shown) using a suitable coupling structure, such as a threaded opening.

When in the assembled state, locking ring 18, slide bearing 24, slide bearing 22, female part 26, ring assembly 27, and adapter plate 42 are coupled as described above. Furthermore, adapter plate 42 may be coupled to a prosthesis. To couple the prosthesis to prosthetic pin 1 using the adapter, the user places pin 1 with body 3 through opening 23 of locking ring 18, through ring assembly 27 into female part 26 until sleeve 4 touches bottom wall 49 of female part 26. At this point, locking ring 18 is in the first position. Thereafter, the user rotates locking ring 18 to the second position. As can be seen in FIG. 1, circumferential portion 33 extends in circumferential direction and in a downward direction. Therefore, when locking ring 18 is rotated, bushings 21C of guiding elements 21 will be guided in circumferential portion 33 whereas bushings 21C of pushing elements 21 will push downwardly on ring assembly 27. Due to this compressive force, resilient rings 29 will deform in a radial direction, thereby providing a radial locking of body 3 of the male part relative to female part 26. At the end of circumferential portion 33, guiding track 31 may display a slight upward movement. If a user rotates locking ring 18 such that bushings 21C pass the connection point where the downwardly and upwardly extending portions of circumferential portion 33 meet, the user may release locking ring 18 without the risk of locking ring 18 rotating back due to the resiliency of rings 29. On the contrary, bushings 21C will be forced against the end of such upwardly extending portion. It should be noted that the upwardly extending portion may be used instead of or in addition to the locking pin.

To align body 3 of the male part relative to female part 26, alignment pins 47 may be used that are inserted through openings 48 and which engage alignment recesses 15 in body 3. Alignment pins 47 may comprise a first part with which pins 47 can be coupled to female part 26, and an engaging part 47A that engages alignment recesses 15. The second part may comprise a resilient member and an engagement member, wherein resilient member provides a biasing force urging engagement member to move away from the first part. When arranging male part 3 inside female part 26, the latter may be rotated relative to female part 26 until the engagement member of alignment pin 47 engages alignment recess 15.

During use, the user may experience an excessive torque applied to the prosthesis, for example as a result of the user falling. When the torque exerted on the prosthesis is sufficiently high to overcome the frictional forces associated with the radial expansion of resilient rings 29, the male part may rotate relative to female part 26. This may or may not include ring assembly 27 rotating relative to female part 26.

The amount of torque that can be applied to the prosthesis without loosing the locking between the male part and female part 26 can be set by appropriately choosing ring assembly 27. For example, by increasing the contribution of resilient rings 29 relative to non-resilient rings 28, the maximum allowable torque can be increased. In this manner, it is possible to adjust the coupling between the male part and female part 26 depending on inter alia the weight of the user and or the nature of his or her daily activities. Alternatively, only a specific ring, i.e. calibration ring 30, may be replaced with a thicker or thinner ring, depending on whether a higher or lower torque threshold is required, respectively.

If the male part has rotated relative to female part 26, the user may push on the locking pin and rotate locking ring 18 from the second position to the first position. In this latter position, the user may relatively easily bring the male part and female part 26 back into alignment. Thereafter, the user may rotate locking ring 18 back to the second position, thereby locking the male part and female part 26.

Figure 6A:
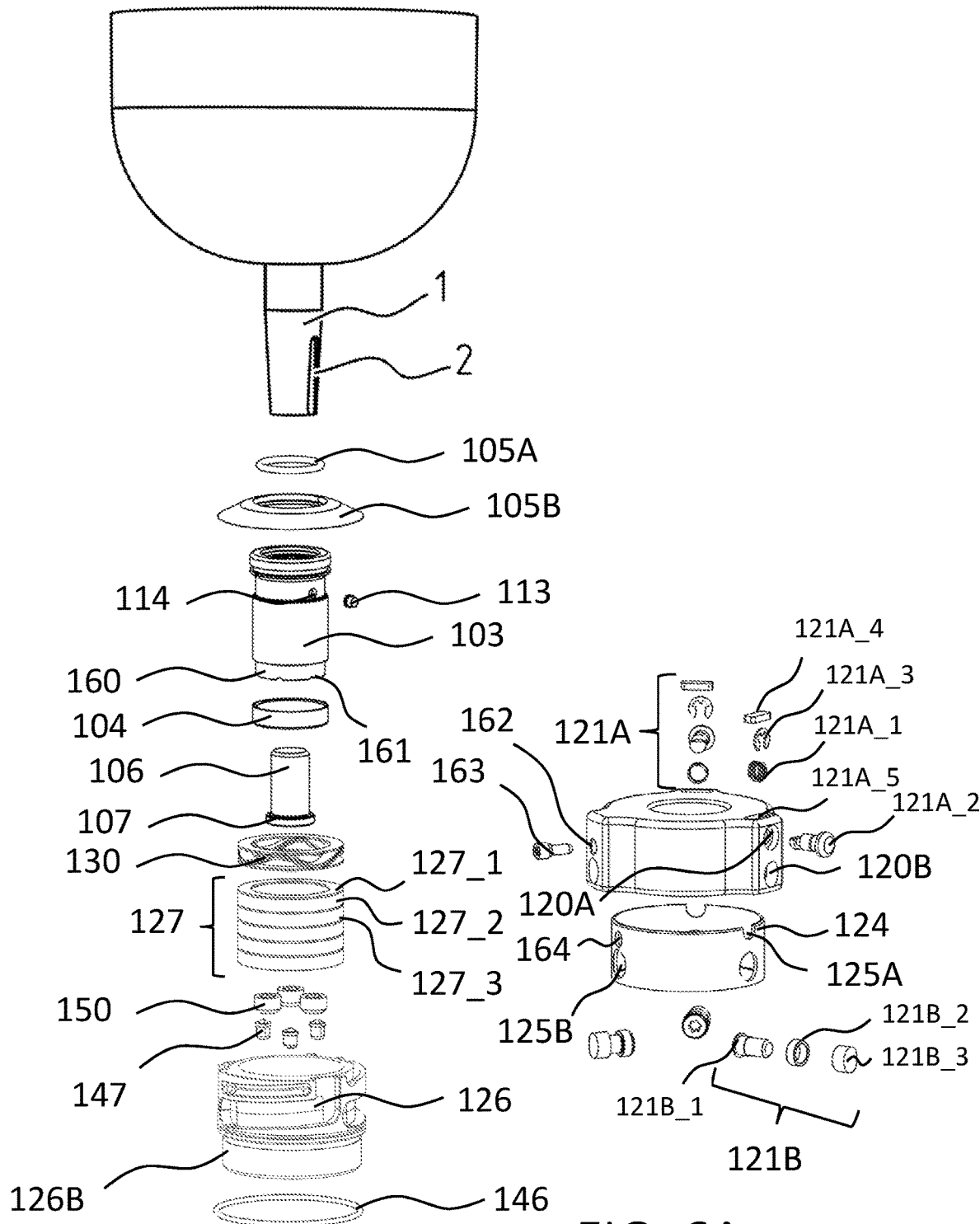
FIGS. 6A and 6B illustrate a partial exploded view of a further embodiment of the adapter in accordance with the present invention.
Figure 6B:
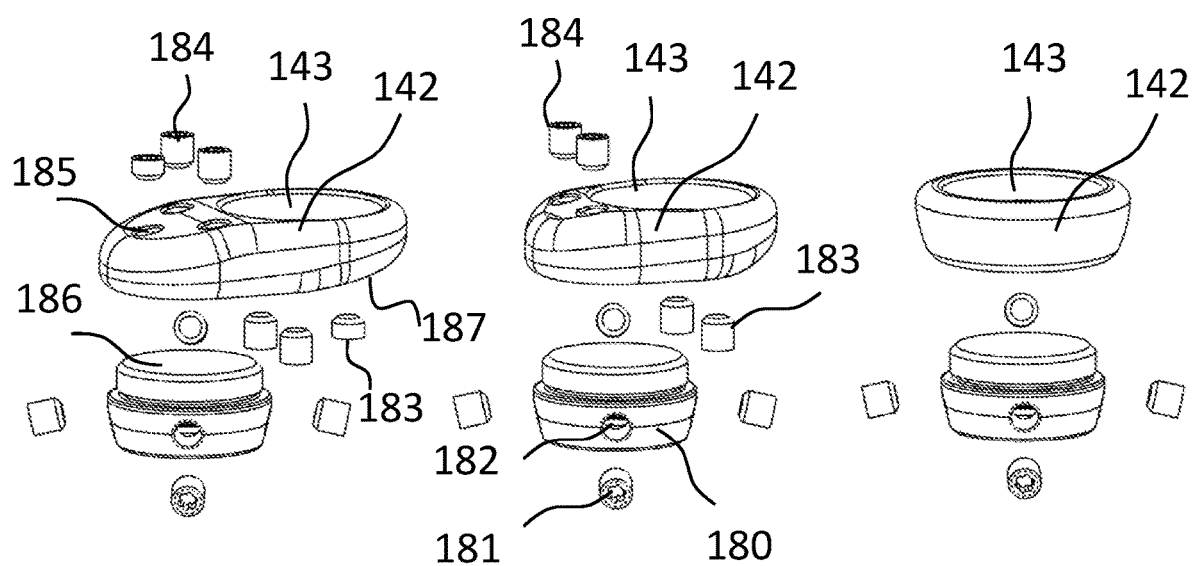

FIGS. 6A and 6B each illustrate a partial exploded view of a further embodiment of the adapter in accordance with the present invention. This adaptor is configured to be coupled to a pin 1 as illustrated in FIGS. 1 and 6A.

Figure 7:
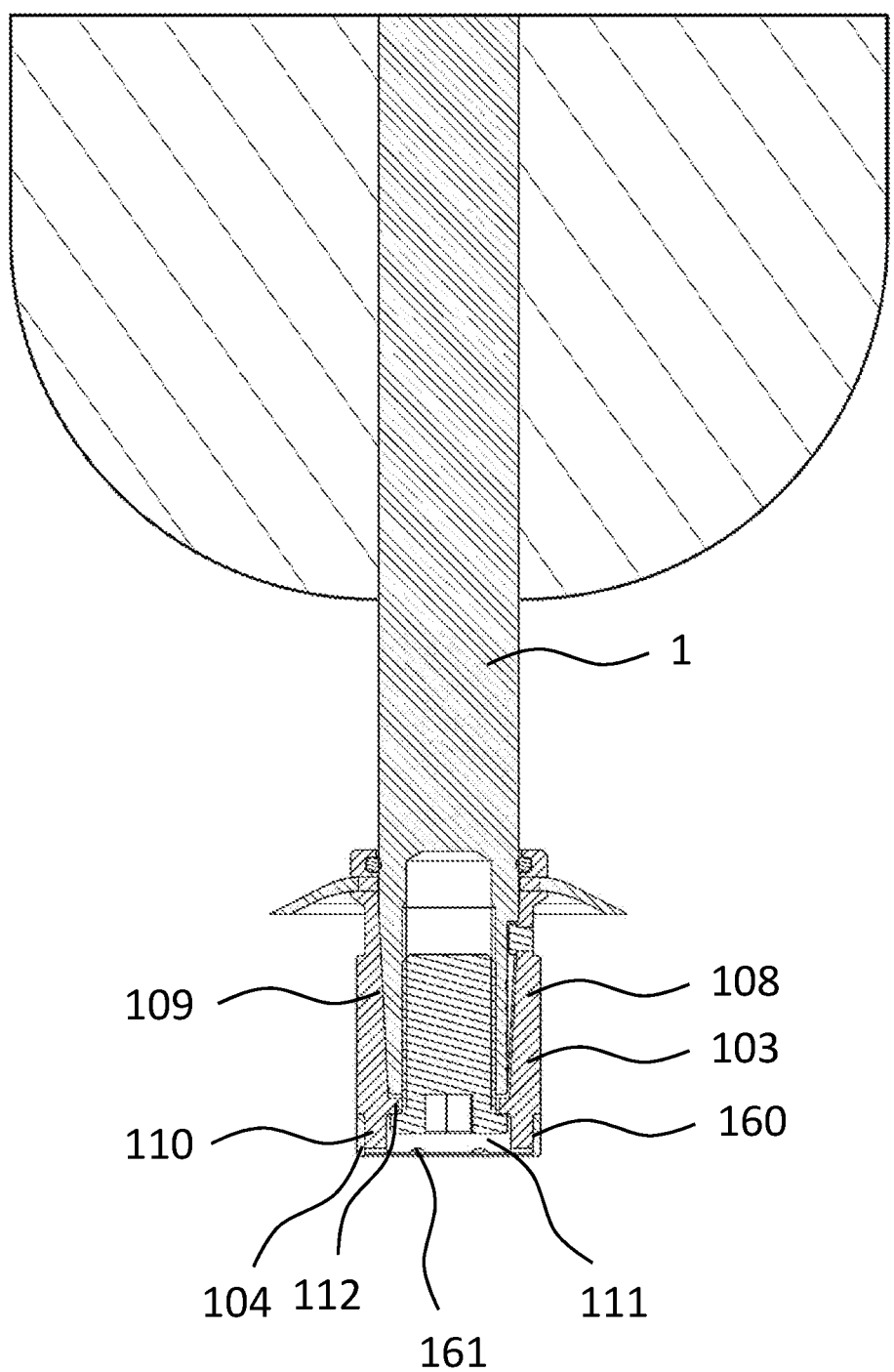
FIG. 7 illustrates a cross sectional view of the male part of the embodiment in FIG. 6A.

This embodiment of the adaptor of the invention comprises a male part consisting of a substantially cylindrical male body 103, a non-metallic sleeve 104, a ring 105A, a ring 105B, and a mounting unit, which in FIG. 6A is embodied as a bolt 106 having a bolt head 107. As can be seen in FIG. 7, a first part 108 of the inner wall of body 103 defines a first cavity 109 of which the wall matches the tapered form of pin 1. A second part 110 of the inner wall defines a second cavity 111 that has a larger diameter than first cavity 109. The transition between parts 108 and 110 defines an edge or rim 112 that can be seen in FIG. 7.

The male part can be coupled to pin 1 by arranging body 103 over pin 1 such that pin 1 is received in first cavity 109 in a form fitted manner. More in particular, first part 108 of the inner wall of body 103 abuts the tapered outer end of pin 1 thereby preventing body 103 to slide even further over pin 1. To secure body 103 to pin 1, at least to prevent it from sliding off pin 1, bolt 106 is arranged through second cavity 111. More in particular, pin 1 has at its end an internal cavity of which the walls are provided with screw thread. A corresponding threading is applied on the outer surface of bolt 106. This allows bolt 106 to be screwed into pin 1. By doing so, bolt head 107 will at a given moment engage rim 112 thereby pushing body 103 upwards.

FIG. 7 further illustrates that sleeve 104 is arranged around recessed portion 160 of body 103. In addition, a bottom rim of body 103 comprises recesses 161 which are used for alignment purposes as will be described later. The lower rim of sleeve 104 extends beyond the lower rim of body 103 to avoid a metal-to-metal contact between the bottom rim of body 103 and female part 126 as will be discussed next.

Ring 105A, which may be of resilient material, provides a sealing of the male part to avoid moisture or dirt to enter in between pin 1 and body 103, whereas ring 105B, which may also be of resilient material, provides a sealing to avoid moisture or dirt to enter female part 126.

To facilitate proper alignment of body 103 relative to pin 1, alignment pin 113, which may or may not be spring biased, penetrates through opening 114 into recess 2 if recess 2 and opening 114 are aligned.

Figure 8A:
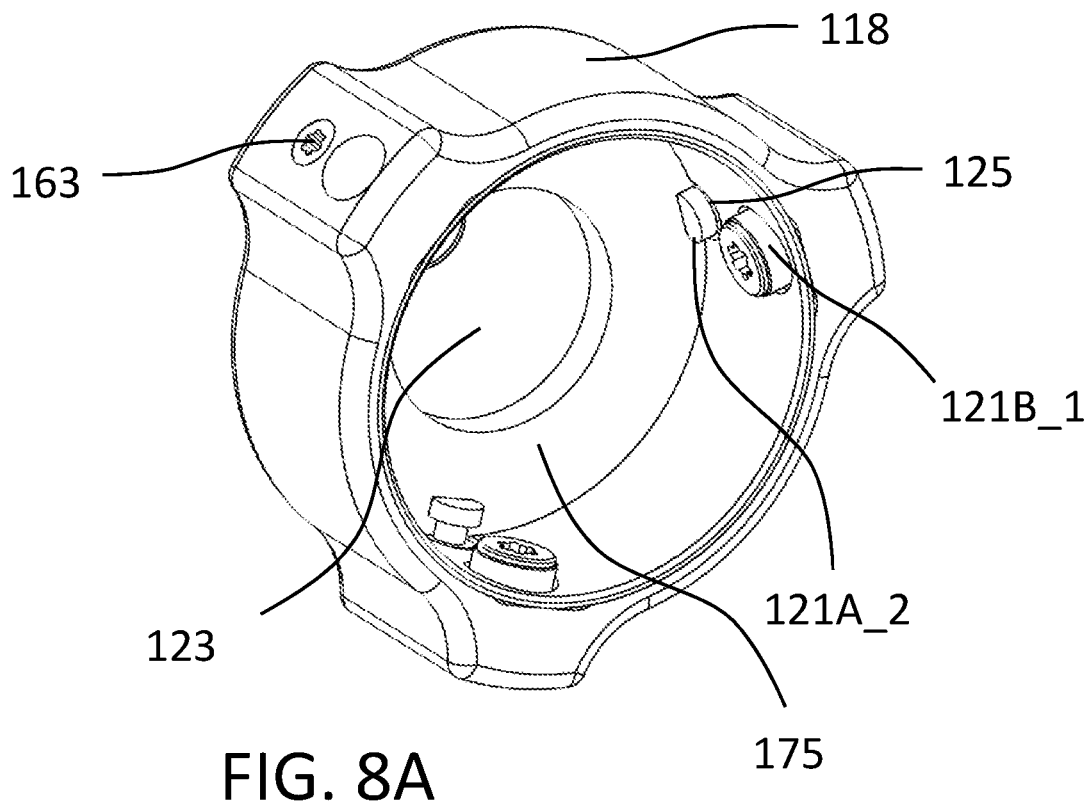
FIGS. 8A and 8B illustrate perspective views of the locking ring of the adapter of FIG. 6A.
Figure 8B:
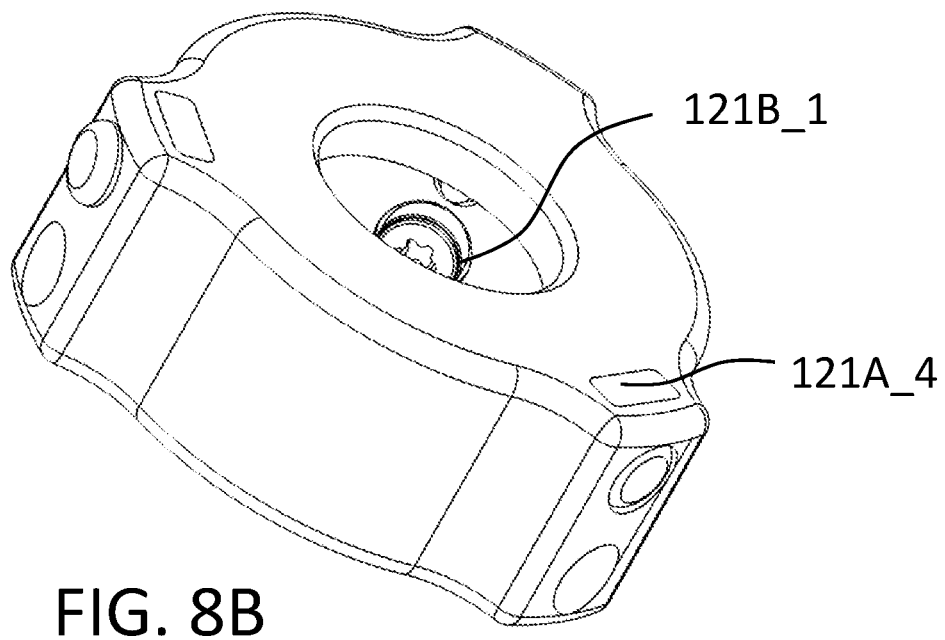

The adapter further comprises a locking ring 118, shown on the right in FIG. 6A and show in perspective views in FIGS. 8A and 8B. A side surface of locking ring 118 is provided with a plurality of openings 120A, 120B, which are arranged at different vertical positions. Elements 121A are inserted through upper openings 120A, whereas elements 121B are inserted through lower openings 120B. A separate opening 162 is provided on the side wall of locking ring 118 through which a locking pin 163 can be fixedly attached.

FIG. 6A further illustrates that the adapter comprises a slide bearing 124 that is to be inserted in locking ring 118 and which prevents direct contact between female part 126, to be discussed later, and locking ring 118. This is shown in more detail in FIG. 8A.

Slide bearing 124 comprises an opening 164 through which locking pin 163 is inserted, openings 125B through which elements 121B are inserted, and recesses 125A allowing the insertion of elements 121A.

FIG. 6A illustrates elements 121A, 121B in exploded view. FIG. 10 illustrates elements 121A in assembled form and FIG. 6A also illustrates elements 121B in assembled form. Elements 121A comprise a pin 121A_2 which is arranged in a cavity between an inner wall and outer wall of locking ring 118. Pin 121A_2 is spring biased using spring 121A_1. To mount pin 121A_2, a spring 121A_1 is inserted into opening 121A_5 to become aligned with opening 120A. Thereafter, pin 121A_2 is inserted through opening 120A, through spring 121A_1 and through opening 125A, which is shown in FIG. 8A. Thereafter, a retaining element 121A_3 is inserted through opening 121A_5 to fixedly engage pin 121A_2. As a result, spring 121A_1 rests on one side against the inner wall of locking ring 108 as it cannot pass through opening 120A and on the other side against retaining element 121A_3. Retaining element 121A_3 ensures that pin 121A_2 cannot disengage from locking ring 118. Moreover, spring 121A_1 urges pin 121A_2 to move outward. After mounting pin 121A_2, opening 121A_5 is closed using a sealing block 121A_4 for protecting against dirt and moisture.

Elements 121B comprises a pin 121B_1, a bush 121B_2 preferably made from ceramic material, and an oval closing cap 121B_3. Closing cap 121B_3 is received in oval opening 120B in a form fitting manner such that closing cap 121B_3 cannot rotate relative to opening 120B.

Pin 121B_1 is arranged through openings 125B and 120B from the inside and is rotationally locked relative to locking ring 118 in a form fitted manner using closing cap 121B_3 to which it is fixedly connected. It should be noted that bush 12113_2 is capable of rotating around pin 121B_1.

Hereinafter, elements 121A which penetrate the upper openings 120A and openings 125A will be designated as positioning elements whereas elements 121B will be designated as guiding elements.

The adapter further comprises a female part 126 that is configured to the male part. Female part 126 is shown in detail in FIG. 9 and FIGS. 10A-10C. Here, it is noted that locking ring 118 is not visible in FIGS. 10A-10C for illustrative purposes.

Inside female part 126, a ring assembly 127 is arranged. This assembly comprises a alternating stack of rings 127_1, 127_2, 127_3. Rings 127_1 are made from a substantially non-resilient material such as stainless steel or a suitable polymer. Rings 127_2, 127_3 are made from a resilient material such as rubber. More in particular, the shore A hardness of these rings may be different. For example, rings 127_2 may have a shore A hardness of about 30-50, whereas rings 127_3 may have a shore A hardness of 70-90.

On top of ring assembly 127 a resilient element 130 is arranged. This element has a relatively high modulus of elasticity in the axial direction of female part 126. Element 130 can take the form of a wave spring, such as a multi-wave spring, a nested wave spring, or the like.

Figure 9:
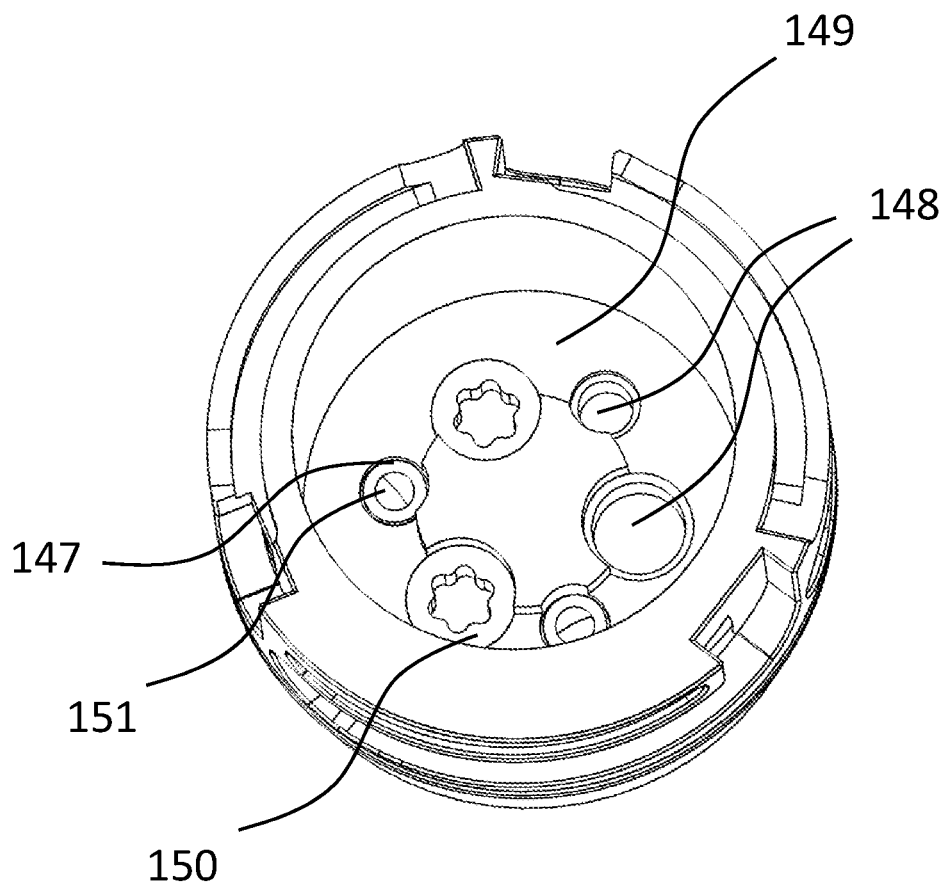
FIG. 9 illustrates a perspective view of the female part of the adapter of FIG. 6A.

When placed in female part 126, ring assembly 127 may rest on a bottom wall 149 of female part 126, as illustrated in FIG. 9. Furthermore, in bottom wall 149, female part 126 may be provided with a plurality of through openings 148 of which some are left open in FIG. 9 for illustrative purposes only. In some of these openings 148, an adjustment screw 150 may be provided.

Other openings 148 are provided with alignment pins 147 that comprise a rotationally mounted ball like element 151 on their top surface. When body 103 is arranged in female part 126, elements 151 can be used to provide predefined alignment positions of body 103 relative to female part 126. In these positions, elements 151 engage recesses 161. Alignment pins 147 may comprise a first part with which pins 147 can be coupled to female part 126.

Figures 10A, 10B, 10C:
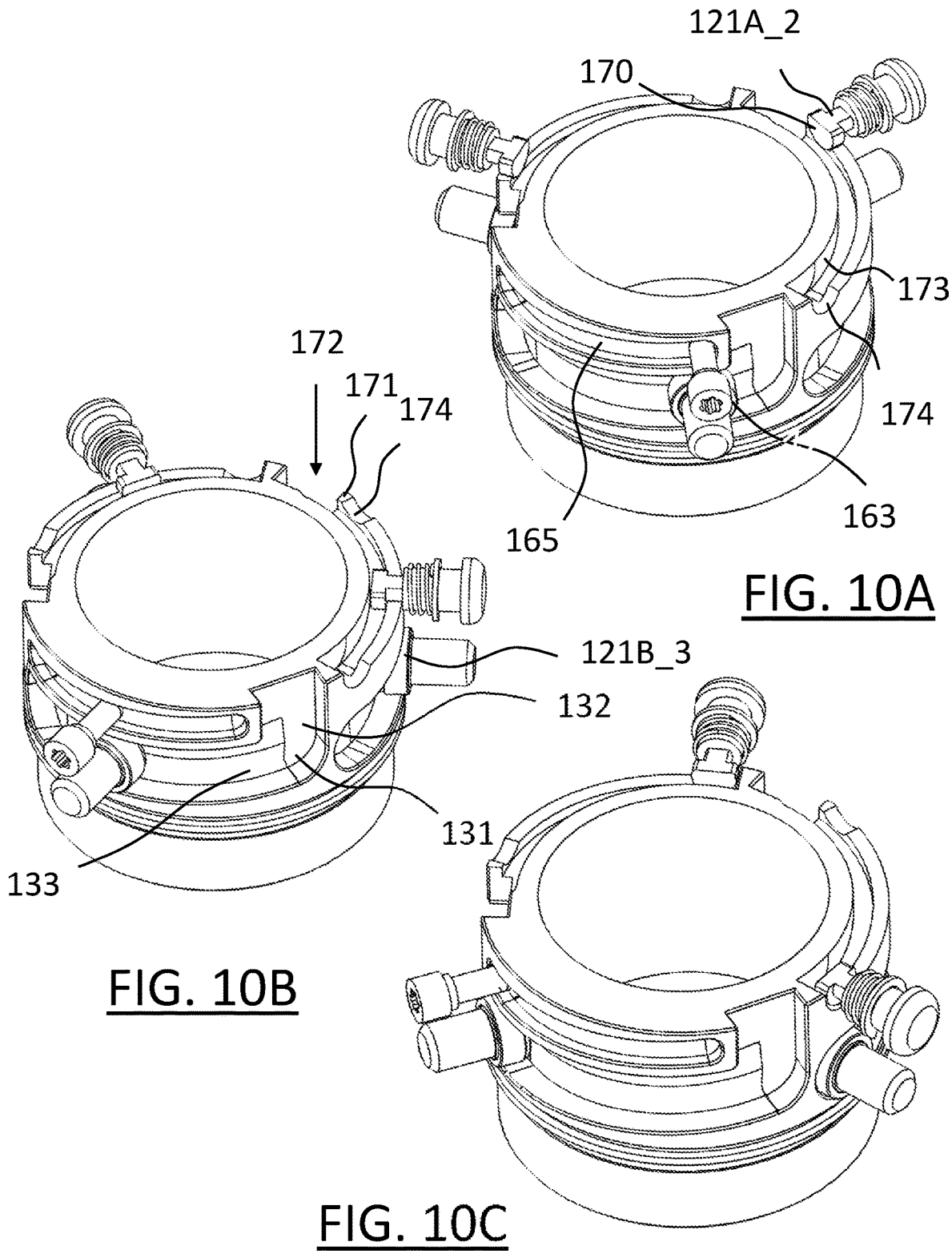
FIGS. 10A-10C illustrate top side perspective views of the locking ring of the adapter of FIG. 1 coupled to the female part.

On a side surface of female part 126, a plurality of guiding tracks 131 is formed, each track 131 comprising a vertical portion 132 extending downwardly from an upper surface of female part 126, and a circumferential portion 133 that partially extends around a side surface of female part 126 in a spiraled manner, see FIGS. 10A-10C. Guiding tracks 131 may be formed by recessing the side surface of female part 126.

Locking ring 118, having slide bearing 124 mounted thereto, can be coupled to female part 126. To that end, guiding elements 121B are aligned with vertical portions 132. Thereafter, locking ring 118 is moved downwardly so that closing cap 121B_3 and bush 121B_2 engage a respective vertical portion 132 and become guided thereby. When the lowest point of vertical portion 132 is reached, locking ring 118 is rotated such that each closing cap 121B_3 and bush 121B_2 engage a respective circumferential portion 131 and become guided thereby.

During the mounting of locking ring 118, positioning elements 121A are pushed inwards. Pins 121A_2 comprise a downward protruding end 170 having a half moon shape. When pushed inward, protruding end 170 is pushed towards inner wall 173 of female part 126. This allows pins 121A_2 to move over edge 171 from vertical slot 172. The positioning of positioning elements 121A and guiding elements 121B is such that when positioning elements 121A are aligned with vertical slots 172, guiding elements 121B are aligned with vertical portions 132.

After locking ring 118 has moved downward and has rotated to allow pins 121B_1 and bushes 121B_2 to engage respective circumferential portions 131, protruding ends 170 are guided in between inner wall 173 and edge 171.

Thereafter, locking pin 163 is mounted such that it engages a locking slot 165. Locking pin 163 thereby limits the rotational movement of locking ring 118 relative to female part 126.

As can be seen from FIGS. 10A-10C, locking ring 118 can be rotated between two states. In the so called open state shown in FIG. 10A, guiding elements 121B are arranged in the upper part of spiral guiding track 131. In this position, protruding ends 170 of positioning elements 121A become aligned with recesses 174 in edge 171. Consequently, under the influence of a spring biasing force, pins 121A_2 move outwardly such that protruding ends 170 engage recesses 174. This provides a locking of locking ring 118 relative to female part 126.

A similar situation occurs in the other state referred to as closed state shown in FIG. 10C. In this position, guiding elements 121B are arranged in the lower part of spiral guiding track 131.

To mount body 103 to female part 126, a user will rotate locking ring 118 to the open state. Thereafter, body 103 is inserted through opening 123 of locking ring 118 into female part 126. A user may then rotate female part 126 relative to body 103 to allow recesses 161 to engage ball like elements 151. This allows the orientation of body 103 relative to female part 126 to be one among several predefined positions.

After aligning body 103 relative to female part 126, the user may operate positioning elements 121A to cause protruding ends 170 to move away from recesses 174 allowing locking ring 118 to be rotated towards the closed position of FIG. 10C. During this motion, elements 121B will move downward in guiding track 131. At the same time, inner wall 175 of locking ring 118, shown in FIG. 8A, will engage the upper surface of resilient element 130. More in particular, the force exerted onto resilient element 130 will continuously increase when moving from the open state to the closed state.

Due to the compressive force, ring assembly 127 will deform radially inward. Consequently, body 103 will be engaged by rings 127_2 and 127_3 thereby locking body 103 relative to female part 126 both radially and axially. The amount of locking can be determined by the composition of rings 127_2 and 127_3, e.g. their hardness, and/or the properties of resilient element 130. In this manner, the clamping force on body 103 and the slipping force or friction at the interface between 103 and ring assembly 127 can be adapted to for example the weight of the user, the regular activities of the user, and/or his or her bone quality.

When a large torque is exerted onto female part 126 relative to body 103, for example when the user has an accident, the frictional force exerted by rings 127_2 and 127_3 onto body 103 may be overcome allowing body 103 to rotate relative to female part 126. At the same time, recesses 161 will disengage from ball like elements 151 which are arranged in alignment pins 147 in a spring biased manner. More in particular, when body 103 rotates relative to female part 126, ball like elements 151 will move inwardly relative to alignment pins 147.

The fact that body 103 may rotate relative to female part 126 prevents inadvertent damage to female part 126, body 103, or pin 1. Hence, the user is able to realign body 103 to female part 126 without the need for seeing a specialized technician and without the risk of surgery which would be required if pin 1 or the mounting thereof in the user's body would become damaged.

FIG. 6B illustrates three different embodiments of an adaptor plate 142 that is to be coupled to female part 126. Each adaptor plate 142 comprises an opening 143 that is provided on an inner side thereof with threading. A corresponding threading is arranged on lower surface 126B of female part 126. In addition, a sealing ring 146 is provided that is arranged in a groove above lower surface 126B to provide a bottom sealing for the coupling between locking ring 118 on the inner surface of slide bearing 124 and female part 126.

Each adaptor plate is to be coupled to a prosthesis mounting element 180 that is provided with an upper surface 186. Mounting element 180 can be coupled to adaptor plate 142 using complementary screw threads. Furthermore, mounting element 180 is provided with a hole on the bottom side in which the prosthesis can be mounted. For all embodiments of adaptor plate 142, the prosthesis can be fixated relative to mounting element 180 using screws 181 that are arranged in through holes 182.

Adaptor plate 142 shown on the left and in the middle in FIG. 6B are provided with a partially closed bottom. This bottom is provided with through holes (not shown) in which adjustments screws 183 can be arranged. When mounting adaptor plate 142 onto female part 126 using the abovementioned screw threads, the final angular position of adaptor plate 142 relative to female part 126 can be adjusted by means of adjustment screws 183 that engage a bottom wall of female part 126. For these same adaptor plates 142, through holes 187 are provided through which further adjustments screws 183 are mounted.

When mounting element 180 is mounted to adaptor plate 142, the angular end position of mounting element 180 relative to adaptor plate 142 can be controlled using adjustment screws 184. More in particular, the angular position of the prosthesis relative to adaptor plate 142 can be controlled using adjustment screws 184 that are inserted in through openings 185 and by which the moment of contact between screws 184 and upper surface 186 of mounting element 180, and therefore the mutual angular position, can be determined.

Adaptor plate 142 shown in FIG. 6B on the right has a through opening 143. Here, the mutual position of mounting element 180 can be controlled using adjustment screws 150, see FIG. 6A and FIG. 9, that directly engage upper surface 186. As explained above, the present invention allows for a secure attachment of a prosthesis to a prosthetic pin while offering a non-destructive protection mechanism to prevent an excessive torque applied between the male and female part damaging the prosthetic pin and the surrounding bony structure.

The present invention has been explained using detailed embodiments thereof. The skilled person will appreciate that various modifications to these embodiments are possible without deviating from the scope of the invention, which is defined by the appended drawings.

LIST OF REFERENCE SIGNS 1 prosthetic pin
2 alignment recess
3 body of the male part
4 sleeve male part
5 ring male part
6 bolt
7 bolt head
8 first part
9 first cavity
10 second part
11 second cavity
12 edge or rim
13 alignment pin
14 opening body male part
15 alignment recess
16 deformable object
17 opening bolt
18 locking ring
19 opening locking ring
19' opening locking ring
20 openings side surface locking ring
21 elements
21A mounting element
21B pin element
21C bushing
22 slide bearing
23 opening locking ring
24 slide bearing
25 opening slide bearing
26 female part
27 ring assembly
28 first rings
29 second rings
30 calibration ring
31 guiding track
32 vertical portion guiding track
33 circumferential portion guiding track
34 recessed portion locking pin
35 non-recessed portion locking pin
36 rim locking pin
37 spring
38 mounting element
39 locking track
40 open portion locking track
41 protruding blocking element
42 adaptor plate
43 opening
44A ring part
44B ring part
45 opening
46 bolt
47 alignment pin
47A engaging part alignment pin
48 opening
49 bottom wall female part
103 body of the male part
104 sleeve
105A sealing ring
105B sealing ring
106 bolt
107 bolt head
108 first part 109 first cavity
110 second part
111 second cavity
112 edge or rim
113 alignment pin
114 opening body male part
118 locking ring
120A upper opening locking ring
120B lower opening locking ring
121A positioning element
121A_1 spring
121A_2 pin
121A_3 retaining element
121A_4 sealing block
121A_5 retaining element
121B guiding element
121B_1 pin
121B_2 bush
121B_3 closing cap
123 opening locking ring
126 female part
127 ring assembly
127_1 ring type 1
127_2 ring type 2
127_3 ring type 3
130 nested wave spring
131 guiding track
132 vertical portion guiding track
133 circumferential portion guiding track
142 adaptor plate
143 opening adaptor plate
146 sealing ring
147 alignment pins
148 opening bottom wall female part
149 bottom wall female part
150 adjustment screw
151 ball alignment pin
160 recess body
161 alignment recess
162 opening locking ring
163 locking pin
164 opening locking bearing
165 locking slot
170 protruding end
171 edge
172 vertical slot
173 inner wall female part
174 recess
175 inner wall locking ring
180 mounting element
181 screw
182 opening
183 adjustment screw
184 adjustment screw
185 hole
186 upper surface mounting element
187 hole

The invention claimed is:

1. Adaptor for mounting a prosthesis, comprising:
a male part configured to be coupled to a prosthetic pin that protrudes from a user's body;
a female part that is configured to be coupled to the prosthesis and to the male part, said female part comprising an elongated cavity; and
a locking ring for locking a rotation of the male part relative to the female part,
wherein the female part further comprises an at least partially resilient ring assembly arranged in the cavity and being configured to expand in a radial direction when the ring assembly is compressed in an axial direction,
wherein the male part can be arranged in or through the ring assembly,
wherein that the locking ring is configured to compress the ring assembly in the axial direction such that the ring assembly expands in the radial direction to thereby lock a rotation of the male part relative to the female part, and
wherein the ring assembly comprises a plurality of first and second rings, wherein the first rings are made from essentially rigid material, wherein the second rings are made from essentially resilient material.

2. The adaptor according to claim 1, wherein the locking ring is coupled to the female part, and wherein the locking ring is movable between a first position, in which position the locking ring exerts no or a relatively low force in the axial direction onto the ring assembly, and a second position, in which the locking ring compresses the ring assembly in the axial direction for said locking of a rotation of the male part relative to the female part.

3. The adaptor according to claim 2, wherein the coupling of the locking ring to the female part is such that a rotation of the locking ring relative to the female part causes an axial displacement of the locking ring relative to the female part to thereby increase or decrease the compression of the ring assembly.

4. The adaptor according to claim 3, wherein an outer wall of the female part comprises one or more guiding tracks, and wherein the locking ring comprises one or more radially inwardly extending guiding elements which are each guided in one of said guiding tracks, the locking ring further comprising one or more pushing elements for pushing in an axial direction onto the ring assembly.

5. The adaptor according to claim 4, further comprising a further resilient element arranged in between the one or more pushing elements and the resilient ring assembly, said further resilient element having a lower modulus of elasticity, preferably a lower Young's modulus, in the axial direction of the female part than in the radial direction, the further resilient element comprising at least one of a wave spring, a multi-wave spring, or a nested wave spring.

6. The adaptor according to claim 4, wherein the one or more pushing elements are formed by an inner wall of the locking ring.

7. The adaptor according to claim 4, wherein the one or more guiding tracks each comprise a spirally extending recess defined in the outer surface of the female part.

8. The adaptor according to claim 7, wherein the lock comprises:
a positioning element mounted in a horizontal direction in the locking ring, said positioning element comprising a positioning pin, and a spring for spring biasing the positioning pin to move outwardly,
wherein the female part comprises an edge having a first recess and a second recess corresponding the first and second position, respectively,
wherein the positioning pin comprises a protruding end,
wherein, when the locking ring is in the first or second position, the positioning pin moves outwardly to engage the first or second recess, respectively, to lock the locking ring in the first or second position, respectively, and wherein, when the locking ring is in an intermediate position between the first and second position, the protruding end is guided in between an inner wall of the female part and said edge.

9. The adaptor according to claim 8, wherein the female part comprises a circumferential locking groove, and wherein the locking ring comprises a locking pin that protrudes through the locking ring and into the circumferential groove, the circumferential groove and locking pin being configured to limit the rotation of the locking ring relative to the female part to prevent the locking ring from getting detached from the female part while the locking pin engages the locking groove.

10. The adaptor according to claim 2, further comprising a lock for locking movement of the locking ring in the first and/or second position.

11. The adaptor according to claim 10, wherein the lock comprises:
- a locking pin having a recessed portion and a non-recessed portion and being mounted in an axial direction in the locking ring;
- a spring for spring biasing the locking pin to urge the locking pin to move in an axial direction; and
- a locking track arranged on an outer wall of the female part, wherein the locking track comprises a radially protruding edge having an open portion,
- wherein, when moving the locking ring between the first and second position, the recessed portion engages the locking track, and wherein, when the locking ring reaches the second position, the spring causes the locking pin to move in the axial direction such that the recessed portion no longer engages the locking track and the non recessed portion abuts the locking track, thereby preventing a rotation of the locking ring from the second position to the first position.

12. The adaptor according to claim 11, wherein, when the locking ring is in the second position, the locking pin protrudes from an upper surface of the locking ring, wherein the locking pin can be pushed in the axial direction to bring the recessed portion back into alignment with the locking track thereby allowing the locking ring to be moved from the second position to the first position.

13. The adaptor according to claim 11, wherein the outer wall of the female part comprises a radially protruding blocking element, wherein, when the locking ring moves from the second to the first position, rotation beyond the first position is prevented by the locking pin engaging the blocking element.

14. The adaptor according to claim 1, wherein the cavity comprises a first part, which exits on an outer surface of the female part facing the locking ring, and a second part adjoining the first part in the axial direction, wherein the first part is wider than the second part, and wherein a transition from the inner wall of the first part to the inner wall of the second part defines a support surface for supporting the ring assembly.

15. The adaptor according to claim 1, wherein the ring assembly comprises a plurality of third rings made from essentially resilient material having a different shore hardness than the second rings.

16. The adaptor according to claim 1, wherein the female part comprises an alignment pin, wherein the male part has an alignment cavity or recess, wherein the alignment pin is configured to engage the recess or cavity for a given angular orientation of the male part relative to the female part.

17. The adaptor according to claim 16, wherein the alignment pin is spring biased to move radially inward into the second part of the cavity, and wherein the alignment pin is configured to move into the recess or cavity for said given angular orientation of the male part relative to the female part.

18. The adaptor according to claim 1, wherein the male part comprises:
- a cavity in which the prosthetic pin can be arranged;
- a radially inwardly extending edge or rim; and
- a mounting unit;
- wherein the mounting unit can be coupled to an inner opening of the prosthetic pin such that an outer end of the mounting unit engages the extending edge or rim for locking a movement in a first direction of the male part relative to the prosthetic pin.

19. The adaptor according to claim 18, wherein the prosthetic pin has a tapered outer shape that matches an inner wall of the male part such that the male part can be form fitted onto the prosthetic pin such that further movement of the male part and the female part in a second direction opposite to the first direction is blocked.

* * * * *